United States Patent [19]

Bushell et al.

[11] Patent Number: 4,942,264

[45] Date of Patent: Jul. 17, 1990

[54] PROCESS FOR THE PREPARATION OF INSECTICIDALLY ACTIVE DIPHENYLETHER COMPOUNDS

[75] Inventors: Michael J. Bushell, Wokingham; Ralph A. Raphael, Barton, both of England

[73] Assignee: Imperial Chemical Industries PLC, London, Great Britain

[21] Appl. No.: 158,232

[22] Filed: Feb. 12, 1988

[30] Foreign Application Priority Data

Feb. 17, 1987 [GB] United Kingdom ............... 8703653

[51] Int. Cl.$^5$ .................. C07C 43/263; A61K 31/085

[52] U.S. Cl. .................................................. 568/635
[58] Field of Search ....................................... 568/635

[56] References Cited

U.S. PATENT DOCUMENTS 4,791,139 12/1988 Bushell et al. ..................... 514/721

Primary Examiner—Anton H. Sutto
Attorney, Agent, or Firm—Cushman, Darby & Cushman

[57] ABSTRACT

This invention relates to a process for the preparation of insecticidally active compounds and to novel styrene derivatives useful as intermediates therein.

1 Claim, No Drawings

PROCESS FOR THE PREPARATION OF INSECTICIDALLY ACTIVE DIPHENYLETHER COMPOUNDS

This invention relates to a process for the preparation of insecticidally active compounds and to novel styrene derivatives useful as intermediates therein.

The applicant's copending UK Patent Application No. 2,187,452 describes insecticidally active diphenyl ether derivatives of formula (I):

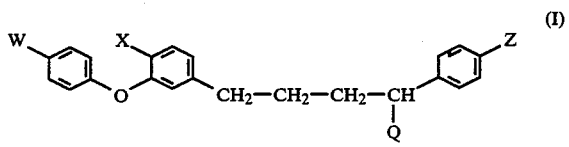
(I)

Wherein X is selected from hydrogen and fluoro, W is selected from hydrogen and halo, Z is selected from halo, alkyl of up to six carbon atoms, alkoxy of up to six carbon atoms, haloalkoxy of up to six carbon atoms and haloalkyl of up to six carbon atoms, and Q is a group of formula $-(CF_2)_n R^1$ where $R^1$ represents hydrogen, chloro or fluoro and n has a value selected from one and two. Preferred insecticidal compounds of formula (I) are those wherein Q represents the trifluoromethyl group.

The compounds of formula (I) may be prepared according to the process described in the UK Patent Application No. 2,187,452 by reduction of the corresponding compound of formula (II):

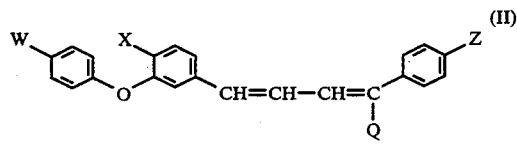
(II)

The applicants have now developed an improved process for the preparation of compounds of formula (I) and formula (II). In a first aspect, therefore, the invention provides a process for the preparation of a compound of formula (I):

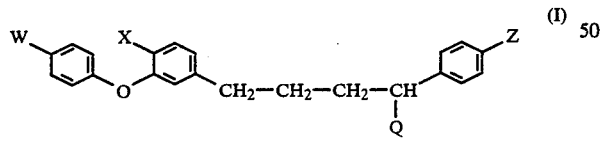
(I)

wherein W is hydrogen or halogen, X is hydrogen or fluoro, Q is a group of formula:

$-(CF_2)_n R^1$ where $R^1$ is hydrogen, fluoro or chloro and n has a value selected from one and two, and Z is halo, alkyl of up to six carbon atoms, alkoxy of up to six carbon atoms, haloalkyl of up to six carbon atoms or haloalkoxy of up to six carbon atoms, which comprises the step of:

(i) Wittig reaction between either (a) a phosphonium salt of formula (III):

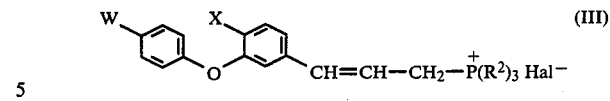
(III)

or (b) a phosphonate of formula (IV):

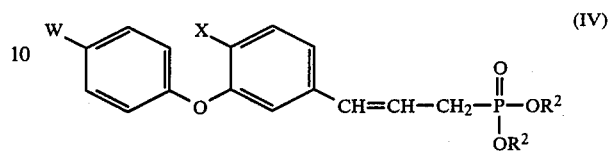
(IV)

wherein W and X have any of the meanings given hereinbefore, $R^2$ represents alkyl of up to six carbon atoms or aryl, preferably methyl, ethyl or phenyl, and $Hal^-$ represents a halide anion, and a ketone of formula (VII):

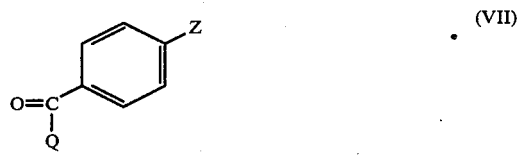
(VII)

wherein Q and Z have any of the meanings given hereinbefore, in the presence of a strong base, for example n-butyllithium, to produce a diene of formula (II):

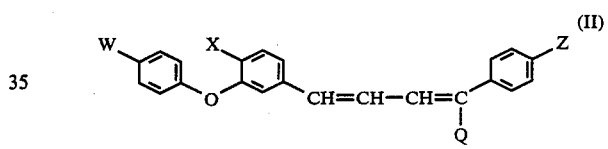
(II)

followed by the step of:

(ii) reaction of the diene of formula (II) with a reducing agent to produce the corresponding compound of formula (I).

The preparation of ketones of formula (VII) is fully described in UK Patent Application No. 2,187,452.

The phosphonium salts of formula (III) and the phosphonates of formula (IV) may be prepared from the corresponding compounds of formula (V):

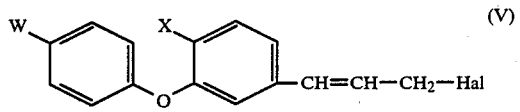
(V)

wherein W and X have any of the meanings given hereinbefore and Hal represents chlorine, bromine or iodine. In a further aspect therefore, the invention provides a process as described hereinbefore for the preparation of a compound of formula (I) wherein the phosphonium salt of formula (III) is prepared by a process which comprises reaction of a compound of formula (V) with a trisubstituted phosphine of formula $P(R^2)_3$, wherein $R^2$ represents alkyl of up to six carbon atoms or aryl; in a preferred aspect, the trisubstituted phosphine is triphenylphosphine. In a further aspect the invention provides a process as described hereinbefore for the preparation of a compound of formula (I) wherein the phosphonate of formula (IV) is prepared by a process which comprises reaction of a compound of formula (V) with a trisubstituted phosphite of formula P(OR$^2$)$_3$, wherein R$^2$ represents alkyl of up to six carbon atoms or aryl; in a preferred aspect, the trisubstituted phosphite is trimethyl phosphite or triethyl phosphite.

The invention also provides a process as described hereinbefore for the preparation of a phosphonium salt of formula (III) or a phosphonate of formula (IV) wherein the compound of formula (V) is prepared by a process which comprises the step of (i):

(i) Reaction between an aldehyde of formula:

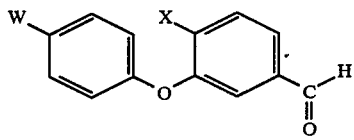

followed by the step of:

(ii) reaction of the compound of formula (VI) with a hydrogen halide selected from hydrogen chloride, hydrogen bromide and hydrogen iodide, to produce the corresponding compound of formula (V).

The reaction of the compound of formula (VI) with a hydrogen halide may be conveniently performed using an inert solvent, for example diethyl ether, previously saturated with gaseous hydrogen chloride, or alternatively in a water miscible solvent, for example tetrahydrofuran, in the presence of a concentrated aqueous solution of a hydrogen halide selected from hydrochloric acid, hydrobromic acid and hydroiodic acid.

The processes described herein are summarised, by way of example only, in Schemes A and B. Further details of the processes are given in the Examples.

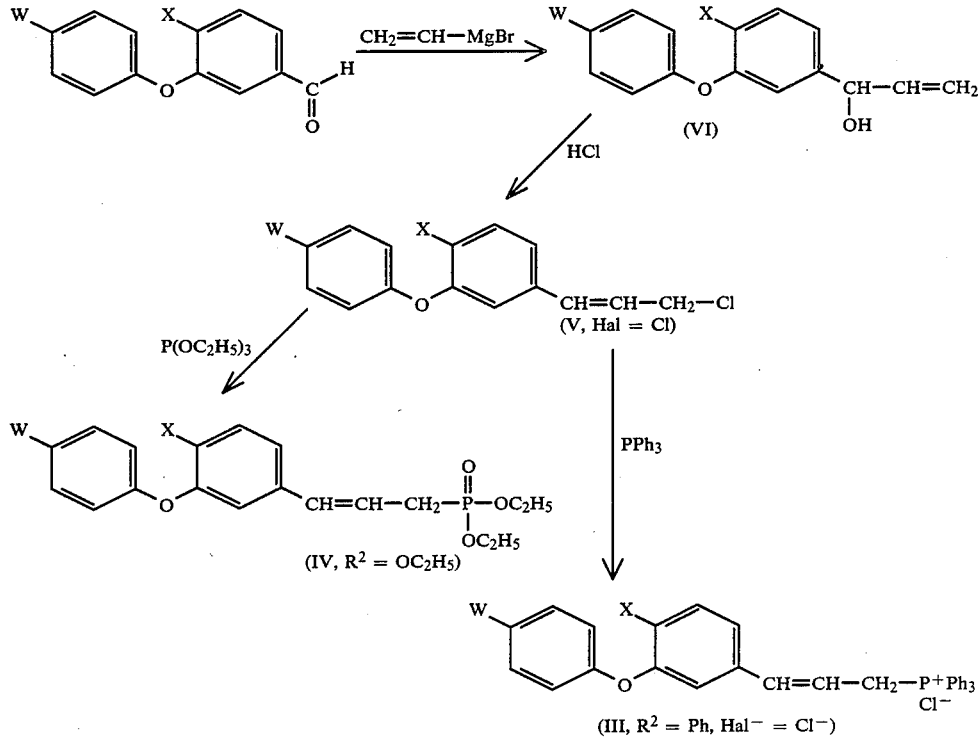

Scheme A wherein W and X have any of the meanings given hereinbefore, and an organometallic vinylating agent, for example vinyllithium or a vinylmagnesium halide of formula:

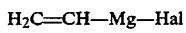

H$_2$C=CH—Mg—Hal wherein Hal represents a halogen atom, preferably bromine, to produce a compound of formula (VI):

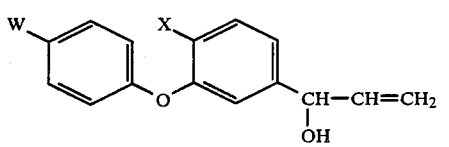

(VI)

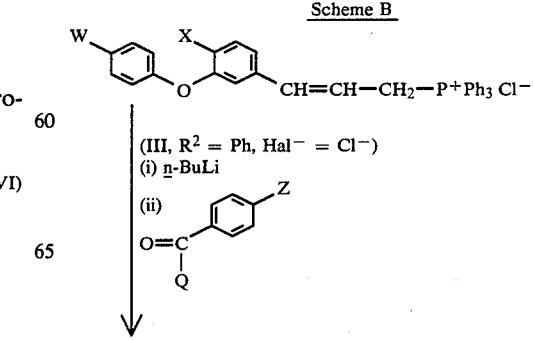

Scheme B (III, R$^2$ = Ph, Hal$^-$ = Cl$^-$)
(i) n-BuLi
(ii)

-continued
Scheme B

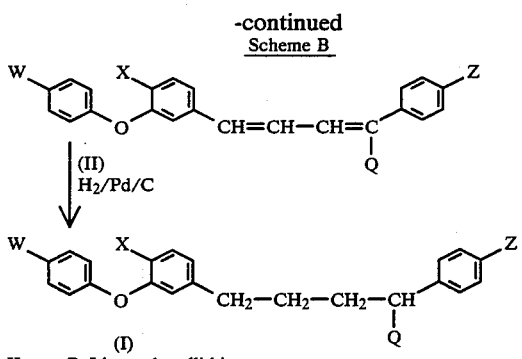

Key: n-BuLi = n-butyllithium
H₂/Pd/C = hydrogenation over a catalyst of Palladium on charcoal.

The compounds of formula (V), (III) and (IV) may exhibit geometric isomerism, and when prepared by the processes of the invention are formed predominantly in the form of the E isomer. Subsequent Wittig reaction to form the compounds of formula (II) retains the initial configuration at the existing carbon-carbon double bond, but may result in a mixture of E and Z configurations at the double bond formed during the Wittig reaction step. In the Examples given hereinafter, the observed ratios of the (E,E) and (E,Z) iosmers of compounds of formula (II) are recorded where they have been determined.

The reduction of compounds of formula (II) to give the compounds of formula (I) may be conveniently carried out by passing hydrogen gas under a pressure of from 1.5 to 20 atmospheres, preferably from 2 to 5 atmospheres, into a solution of the compound of formula (II) in a suitable solvent such as a lower alkanol, for example methanol or ethanol. The presence of an asymmetric carbon atom in the compounds of formula (I) leads to the possibility of stereoisomerism. Reduction of the compounds of formula (II) by hydrogenation as described herein usually produces a racemic mixture of the R and S enantiomers of the corresponding compound of formula (I). Enantiomeric excess of one enantiomer may result from the use of a chiral catalytic reducing agent. In those compounds of formula (I) where the group $R^1$ represents hydrogen or chloro, hydrogenation may lead to the formation of side products resulting from competing reductive dehalogenation in the group Q.

Examples of the compounds of formula (I) which may be prepared by the processes of the invention are given in Table I.

TABLE I

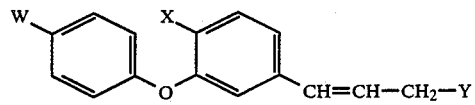

| COMPOUND NO. | W | X | Q | Z |
|---|---|---|---|---|
| 1 | H | H | CF₃ | OC₂H₅ |
| 2 | H | F | CF₃ | OC₂H₅ |
| 3 | H | H | CF₃ | C(CH₃)₃ |
| 4 | H | H | CF₃ | OCF₃ |
| 5 | H | H | C₂F₅ | OC₂H₅ |
| 6 | H | Cl | CF₃ | Cl |
| 7 | F | H | CF₃ | OC₂H₅ |
| 8 | H | H | CF₃ | CF₃ |
| 9 | H | F | CF₃ | CF₃ |
| 10 | H | F | CF₃ | OCF₃ |

TABLE I-continued

| COMPOUND NO. | W | X | Q | Z |
|---|---|---|---|---|
| 11 | Cl | F | CF₃ | CF₃ |
| 12 | Br | F | CF₃ | OC₂H₅ |
| 13 | H | F | CF₂H | OCF₃ |
| 14 | H | H | CF₂Cl | OCF₃ |
| 15 | H | H | CF₂H | OC₂H₅ |
| 16 | H | H | CF₂H | OCF₃ |
| 17 | Cl | H | CF₃ | OC₂H₅ |
| 18 | Cl | H | CF₃ | OCF₃ |
| 19 | Cl | F | CF₃ | OC₂H₅ |
| 20 | Cl | F | CF₃ | OCF₃ |
| 21 | H | H | CF₃ | Cl |
| 22 | Cl | F | CF₃ | Cl |
| 23 | H | F | CF₃ | Cl |

The intermediates of formulae (III), (IV) and (V) are believed to be novel. In a further aspect, therefore, the invention provides compounds of formula:

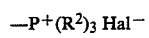

and geometric isomers thereof, wherein W and X have any of the meanings given hereinabove, and Y represents chlorine, bromine or iodine, or Y is selected from a group of formula:

$-P^+(R^2)_3$ Hal$^-$ a group of formula

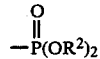

wherein $R^2$ represents alkyl of up to six carbon atoms or aryl and Hal$^-$ represents a halide anion. Specific examples of compounds of formulae (III), (IV) and (V) provided by the invention include:

E-3-(3-phenoxyphenyl)-1-chloroprop-2-ene,
E-3-(3-phenoxyphenyl)-1-bromoprop-2-ene,
E-3-(4-fluoro-3-phenoxyphenyl)-1-chloroprop-2-ene,
E-3-[3-(4-chlorophenoxy)phenyl]-1-chloroprop-2-ene,
E-3-(3-phenoxyphenyl)prop-2-en-1-yl triphenyl phosphonium chloride,
E-3-(4-fluoro-3-phenoxyphenyl)prop-2-en-1-yl triphenyl phosphonium chloride,
E-3-[3-(4-chlorophenoxy)phenyl]prop-2-en-1-yl triphenyl phosphonium chloride,
dimethyl E-3-(4-fluoro-3-phenoxyphenyl)prop-2-en-1-yl phosphonate.

The following Examples illustrate various aspects of this invention. In the Examples the products were usually identified and characterised by means of nuclear magnetic reasonance spectroscopy and infra red spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, $^1$H Nuclear Magnetic Resonance (NMR) spectrometry was performed at a frequency of 270 MHz on a Jeol FX 270 NMR spectrometer, unless otherwise indicated. 90 MHz, 60 MHz and 400 MHz $^1$H NMR spectrometry were performed using Jeol FX 90Q, Jeol PMX 60SI and Jeol GX400 spectrometers respectively.

$^{19}$F NMR spectrometry was performed on a Jeol FX90Q spectrometer at a frequency of 84.26 MHz. All NMR shift values ($\delta$) are quoted in ppm relative to a standard (TMS or CFCl$_3$).

Molecular Ion (M$^+$) peaks were determined on one of three mass spectrometers: Jeol DX303, Kratos MS80 or Hewlett Packard HP 5992.

EXAMPLE 1

This Example illustrates the stages in the preparation of E-3-(4-fluoro-3-phenoxyphenyl)prop-2-en-1-yl triphenyl phosphonium chloride.

Stage 1: Preparation of 1-(4-fluoro-3-phenoxyphenyl)prop-2-en-1-ol

A solution of 4-fluoro-3-phenoxybenzaldehyde (35 g) in dry tetrahydrofuran (100 cm$^3$) was added slowly to stirred vinyl magnesium bromide, commercially available from the Aldrich Chemical Co Ltd, Gillingham, Dorset, England, (162 cm$^3$ of a 1.0 molar solution in tetrahydrofuran) under an atmosphere of nitrogen at the ambient temperature (ca 20° C.); a moderate exotherm was noted, raising the temperature of the mixture to 40° C. On completion of the addition, the mixture was stirred for a further 2 hours, then poured into water and acidified with dilute hydrochloric acid. The products were extracted three times into ethyl acetate and the combined organic layers were washed with water, dried over anhydrous magnesium sulphate and concentrated by evaporation under reduced pressure to give a viscous oil (39 g), characterised as 1-(4-fluoro-3-phenoxyphenyl)prop-2-en-1-ol, 97% pure by gas liquid chromatographic analysis.

400 MHz $^1$H NMR (CDCl$_3$) $\delta$ (ppm): ca 2.3 (1H, broad); 5.11 (1H,dd, J=10 Hz,1 Hz); 5.18 (1H,dt, J=10 Hz, 1 Hz); 5.3 (1H,dt, J=17 Hz, 1 Hz); ca 5.95 (1H,m); 6.9–7.4 (8 H,m).

Stage 2: Preparation of E-3-(4-fluoro-3-phenoxyphenyl)-1-chloroprop-2-ene 1-(4-Fluoro-3-phenoxyphenyl)prop-2-en-1-ol (38 g) was dissolved in tetrahydrofuran (400 cm$^3$) and concentrated hydrochloric acid (180 cm$^3$) was added with vigorous stirring. Stirring was continued for a further 2 hours, after which time, analysis of a withdrawn sample by gas liquid chromatography showed no starting material remaining. The mixture was diluted with water and the products extracted into ethyl acetate. The combined organic layers were washed with water (4 times), then dried over anhydrous magnesium sulphate. Evaporation of the solvent under reduced pressure gave E-3-(4-fluoro-3-phenoxyphenyl)-1-chloroprop-2-ene (44 g) as a viscous oil, 98% pure by gas liquid chromatographic analysis.

An alternative preparative method is described in Stage 2 of Example 2(i). The preparation of brominated analogues is described in Example 2(ii).

$^1$H NMR (CDCl$_3$) $\delta$ (ppm): 4.19 (2H,d); ca 6.15 (1H,dt); ca 6.55 (1H,d); 6.9–7.4 (8H,m).

The E configuration was assigned after consideration of the coupling constants in the NMR spectrum.

Stage 3: Preparation of E-3-(4-fluoro-3-phenoxyphenyl)prop-2-en-1-yl triphenyl phosphonium chloride.

A mixture of E-3-(4-fluoro-3-phenoxyphenyl)-1-chloroprop-2-ene (42 g), triphenylphosphine (42 g) and xylene (300 cm$^3$) was heated at the reflux temperature for 16 hours. After cooling, crystals of E-3-(4-fluoro-3-phenoxyphenyl)prop-2-en-1-yl triphenyl phosphonium chloride (68 g) were filtered from the reaction mixture, washed with dry diethyl ether, dried by suction and stored in a desiccator under vacuum.

$^1$H NMR (DMSO) $\delta$ (ppm): ca 4.65 (2H,m); 6.0 (1H,broad m); 6.55 (1H,dd); 6.9–7.4 (8H,m); 7.7–7.9 (15H,m).

EXAMPLE 2

The following compounds were prepared from the appropriate starting materials by procedures similar to those described in Example 1.

(i) E-3-(3-phenoxyphenyl)prop-2-en-1-yl triphenyl phosphonium chloride

Stage 1: 1-(3-phenoxyphenyl)prop-2-en-1-ol $^1$H NMR (CDCl$_3$) $\delta$ (ppm): 1.93 (1H, broad), 5.18 (1H, broad s); ca 5.21 (1H, dd); 5.38 (1H, dd); 6.04 (1H, octet); 6.9–7.4 (9H, m).

Stage 2: E-3-(3-phenoxyphenyl)-1-chloroprop-2-ene

Alternative Method 1-(3-Phenoxyphenyl)prop-2-en-1-ol (0.05 g) was dissolved in diethyl ether (2 cm$^3$) which had been previously saturated with hydrogen chloride gas, and the solution was stirred at the ambient temperature for 2 hours. Water was added to the mixture and the products extracted into further diethyl ether. The combined ethereal layers were dried over anhydrous magnesium sulphate and the solvent evaporated under reduced pressure. The residual oil was purified by column chromatography on a silica gel support, eluted with hexane containing 5% by volume ethyl acetate, to give E-3-(3-phenoxyphenyl)-1-chloroprop-2-ene (0.03 g).

$^1$H NMR $\delta$ (ppm): 4.21 (2H, d); 6.1–6.4 (1H, dt); ca 6.6 (1H, d); 6.8–7.45 (9H, m).

Stage 3: E-3-(3-Phenoxyphenyl)prop-2-en-1-yl triphenyl phosphonium chloride.

$^1$H NMR (CDCl$_3$) $\delta$ (ppm): ca 4.7 (1H, m); ca 6.1 (1H, m); 6.5 (1H, dd); 6.8–7.4 (9H, m); 7.65–7.9 (15H, m).

(ii) E-3-(3-phenoxyphenyl)-1-bromoprop-2-ene may be prepared from 1-(3-phenoxyphenyl)prop-2-en-1-ol according to the method of Stage 2 of Example 1 using 48% aqueous hydrobromic acid solution in place of concentrated hydrochloric acid.

$^1$H NMR (CDCl$_3$) $\delta$ (ppm): ca 4.1 (2H,d,J=7 Hz); 6.0–6.5 (2H,dt,J=17 Hz and 7 Hz); ca 6.6 (1H,d,J=17 Hz); 6.8–7.5 (9H,m, aromatic protons).

(iii) E-3-[3-(4-chlorophenoxy)phenyl]prop-2-en-1-yl triphenyl phosphonium chloride.

Stage 1: 1-[3-(4-chlorophenoxy)phenyl]prop-2-en-1-ol $^1$H NMR (CDCl$_3$) $\delta$ (ppm): 1.96 (1H, broad s); ca 5.2 (2×$^1$H overlapping); 5.36 (1H,d); 6.0 (1H,ddd); 6.9–7.4 (8H,m, aromatic protons)

Stage 2:
E-3-[3-(4-chlorophenoxy)phenyl]-1-chloroprop-2-ene $^1$H NMR (CDCl$_3$) δ (ppm): 4.21 (2H,d); ca 6.3 (1H,dt); 6.6 (1H,d); 6.9–7.4 (8H,m).

Stage 3:
E-3-[3-(4-chlorophenoxy)phenyl]prop-2-en-1-yl triphenyl phosphonium chloride $^1$H NMR (CDCl$_3$) δ (ppm): 4.7 (2H,dd); ca 6.1 (1H,m); ca. 6.53 (1H,dd); 6.8–7.4 (8H,m); 7.6–8.0 (15H,m)

EXAMPLE 3

This Example illustrate the preparation of 1,1,1-trifluoro-2-(4-trifluoromethoxyphenyl)-5-(3-phenoxyphenyl)penta-2,4-diene as a 6:1 mixture of the 2E,4E) and (2Z,4E) isomers.

n-Butyllithium (6.4 cm$^3$ of a 2.5M solution in n-hexane) was added dropwise to a cooled (0° C.) suspension of E-3-(3-phenoxyphenyl)prop-2-en-1-yl triphenyl phosphonium chloride (8.2 g) in dry tetrahydrofuran (100 cm$^3$); a dark red colour developed in the reaction mixture. The reaction mixture was stirred at 0° C. for a further 30 minutes, then a solution of 4-trifluoromethoxy-α,α,α-trifluoroacetophenone (3.87 g) in dry tetrahydrofuran (50 cm$^3$) was added dropwise. The mixture was allowed to stir for a further hour and was then poured into water, and the products extracted into diethyl ether. The combined organic layers were washed with water, dried over anhydrous magnesium sulphate and concentrated by evaporation under reduced pressure. The residue was mixed with silica gel and diethyl ether and evaporated. The residue was placed on top of a short plug of silica, and products were eluted by washing with n-hexane containing 10% by volume diethyl ether. Evaporation under reduced pressure gave an oil, which was purified by high pressure liquid chromatography, using n-hexane containing 10% by volume dichloromethane as eluent to give the title compound as a 6:1 mixture of the (2E,4E) and (2Z,4E) isomers (4.24 g). High pressure liquid chromatography using n-hexane containing 1% by volume ethyl acetate allowed separation and isolation of the major (2E,4E) isomer of 96% purity.

$^1$H NMR (CDCl$_3$) δ (ppm) for 2E,4E isomer: 6.55 (1H,dd); 6.8–7.4 (15H,m).

$^{19}$F NMR (CDCl$_3$) δ (ppm - relative to CFCl$_3$) for isomer mixture: −56.88 (E isomer CF$_3$,s); −58.18 and −58.33 (CF$_3$O, 2s); −65.2 (Z isomer CF$_3$,s).

EXAMPLE 4

The following compounds were prepared from the appropriate starting materials by a procedure similar to that described in Example 3.

(i) 1,1,1-Trifluoro-2-(4-trifluoromethoxyphenyl)-5-(4-fluoro-3-phenoxyphenyl)penta-2,4-diene as an 85:15 mixture of the (2E,4E) and (2Z,4E) isomers from 4-trifluoromethoxy-α,α,α-trifluoroacetophenone and 3-(4-fluoro-3-phenoxyphenyl)-prop-2-en-1-yl triphenyl phosphonium chloride.

The 85:15 isomer mixture was separated by chromatography to give (A) the pure (2E,4E) isomer and (B) a 1:1 mixture of the (2E,4E) and (2Z,4E) isomers.

(A) (2E,4E) isomer: $^1$H NMR (CDCl$_3$) δ (ppm): 6.45 (1H,dd); 6.78 (1H,d); 6.9–7.4 (13H,m).

(B) contains extra peaks in the alkene region for the Z-isomer (ca 6.65).

(ii) 1,1-Difluoro-1-chloro-2-(4-trifluoromethoxyphenyl)-5-(4-fluoro-3-phenoxyphenyl)penta-2,4-diene as 12:1 mixture of (2E,4E) and (2Z,4E) isomers, from 4-trifluoromethoxy- α, α-difluoro-α-chloroacetophenone and 3-(4-fluoro-3-phenoxyphenyl)prop-2-en-1-yl triphenyl phosphonium chloride.

$^1$H NMR (CDCl$_3$) δ (ppm): 6.32 (dd) and 6.77 (d). (2E,4E isomer); 6.45 (d) and 6.7(d) (2Z,4E isomer); 6.9–7.5 (m)

(iii) 1,1-Difluoro-2-(4-ethoxyphenyl)-5-(3-phenoxyphenyl)penta-2,4-diene, as a 3:1 mixture of the (2E,4E) and (2Z,4E) isomers, from 4-ethoxy-α,α-difluoroacetophenone and 3-(3-phenoxyphenyl)prop-2-en-1-yl triphenyl phosphonium chloride.

$^1$H NMR (CDCl$_3$) δ (ppm): ca 1.4 (3H,overlapping t); ca 4.1 (2H,overlapping g); 6.26 (1H,t,J=56 Hz); 6.6–7.4 (16H,m)

(iv) 1,1-Difluoro-1-chloro-2-(4-ethoxyphenyl)-5-(3-phenoxyphenyl)penta-2,4-diene as a 4:1 mixture of the (2E,4E) and (2Z,4E) isomers, from 4-ethoxy-α,α-difluoro-α-chloroacetophenone and 3-(3-phenoxyphenyl)prop-2-en-1-yl triphenyl phosphonium chloride.

$^1$H NMR (CDCl$_3$) δ (ppm): ca 1.45 (3H,overlapping t); ca 4.10 (2H,overlapping g); 6.4–7.4 (16H,m)

$^{19}$F NMR (CDCl$_3$) δ (ppm - relative to CFCl$_3$) −43.9, −51.3 (CF$_2$Cl, 2s, in ratio 1:4)

(NB. Product contained some unreacted acetophenone which could be removed by heating under vacuum)

(v) 1,1-Difluoro-1-chloro-2-(4-trifluoromethoxyphenyl)-5-(3-phenoxyphenyl)penta-2,4-diene as a 13:1 mixture of the (2E,4E) and (2Z,4E) isomers, from 4-trifluoromethoxy-α,α-difluoro-α-chloroacetophenone and 3-(3-phenoxyphenyl)prop-2-en-1-yl triphenyl phosphonium chloride.

(2E,4E) isomer separated by high pressure liquid chromatography (93% pure)

$^1$H NMR (CDCl$_3$) δ (ppm): 6.44 (1H,dd); 6.8–7.4 (15H,m)

Molecular ion: 466/468

(vi) 1,1,1-Trifluoro-2-(4-trifluoromethoxyphenyl)-5-[3-(4-chlorophenoxy)phenylpenta-2,4-diene as a 7.5:1 mixture of the (2E,4E) and (2Z,4E) isomers, from 4-trifluoromethoxy-α,α,α-trifluoroacetophenone and 3-[3-(4-chlorophenoxy)phenyl]prop-2-en-1-yl triphenyl phosphonium chloride.

$^1$H NMR (CDCl$_3$) δ (ppm): Olefinic and aromatic protons in range of 6.5–7.4

$^{19}$F NMR (CDCl$_3$) δ (ppm - relative to CFCl$_3$): −58.2 (CF$_3$O,s,Z-isomer); −58.4 (CF$_3$O,s,E-isomer); −65.3 (CF$_3$,s,Z-isomer); −56.9 (CF$_3$,s,E-isomer)

Integration shows ratio of (2E,4E) and (2Z,4E) isomers to be 7.5:1

EXAMPLE 5

This Example illustrates the preparation of dimethyl E-3-(4-fluoro-3-phenoxyphenyl)prop-2-en-1-yl phosphonate.

A mixture of E-3-(4-fluoro-3-phenoxyphenyl)-1-chloroprop-2-ene (1g) and trimethyl phosphite (0.95 g) was heated at 125° C. under an atmosphere of nitrogen for 6 hours. Analysis by gas liquid chromatography showed complete reaction at this stage. The mixture was cooled and poured into water, and the products were extracted into chloroform. The combined organic layers were washed twice with water, dried over anhydrous magnesium sulphate and concentrated to leave dimethyl E-3-(4-fluoro-3-phenoxyphenyl)prop-2-en-1-yl phosphonate as an oil (1.3 g).

¹H NMR (CDCl₃) δ (ppm): 2.73 (2H,dd and fine coupling); 3.74 (6H,d); 6.0 (1H,m); 6.42 (1H,dd); 6.9–7.4 (8H,m).

EXAMPLE 6

This Example describes the preparation of 1,1-difluoro-1-chloro-2-(4-trifluoromethoxyphenyl)-5-(3-phenoxy-4-fluorophenyl)penta-2,4-diene as a 2:1 mixture of the (2E,4E) and (2Z,4E) isomers.

n-Butyllithium (0.24 cm³ of a 2.5 molar solution in hexane) was added dropwise to a solution of dimethyl E-3-(4-fluoro-3-phenoxyphenyl)prop-2-en-1-yl phosphonate (0.2 g) in dry tetrahydrofuran (5 cm³) at the ambient temperature, under an atmosphere of nitrogen; a deep red colouration was produced. After stirring for 2 hours at the ambient temperature, a solution of 4-trifluoromethoxy-α,α-difluoro-α-chloroacetophenone (0.164 g) in tetrahydrofuran (2 cm³) was added dropwise. Gas liquid chromatography after 30 minutes showed no starting materials present. The mixture was quenched with water and the products extracted into chloroform. The organic layers were dried and concentrated by evaporation under reduced pressure to give a mixture of two isomers of the title compound, confirmed by comparison with an authentic sample of the title compound produced by an alternative route as the (2E,4E) and (2Z,4E) isomers in a 2:1 ratio.

EXAMPLE 7

This Example illustrates the preparation of 1,1,1-trifluoro-2-(4-trifluoromethoxyphenyl)-5-(3-phenoxyphenyl)pentane.

The (2E, 4E) isomer of 1,1,1-trifluoro-2-(4-trifluoromethoxyphenyl)-5-(3-phenoxyphenyl)penta-2,4-diene (2.7 g) in ethanol (80 cm³) in the presence of a hydrogenation catalyst (10% palladium on charcoal, 200 mg) was stirred under an atmosphere of hydrogen at a pressure of 3.7 atmospheres for 1 hour. The reaction mixture was filtered through celite to remove the catalyst and the celite washed with further ethanol. The combined filtrates were concentrated by evaporation of the ethanol under reduced pressure to yield 1,1,1-trifluoro-2-(4-trifluoromethoxyphenyl)-5-(3-phenoxyphenyl)pentane (2.09 g) as a colourless oil.

¹H NMR (CDCl₃)δ: ca 1.48 (2H, m); 1.84 and 2.0 (2H, broad m); 2.56 (2H, m); 3.22 (1H, broad m); 6.7–7.4 (13H, m).

¹⁹F NMR (CDCl₃) δ(ppm - relative to CFCl₃): −58.33 (CF₃O, s), −70.41 (CF₃, d).

EXAMPLE 8

The following compounds were prepared from the appropriate alkadiene by a procedure similar to that described in Example 7.

(i) 1,1,1-Trifluoro-2-(4-trifluoromethoxyphenyl)-5-(4-fluoro-3-phenoxyphenyl)pentane, from 1,1,1-trifluoro-2-(4-trifluoromethoxyphenyl)-5-(4-fluoro-3-phenoxyphenyl)penta-2,4-diene.

¹H NMR (CDCl₃) δ (ppm): ca 1.5 (2H, m); 1.8, 2.0 (2H, broad, m); 2.55 (2H, m); 3.2 (1H, m); 6.7–7.4 (12H, m).

¹⁹F NMR (CDCl₃) δ (ppm - relative to CFCl₃): =58.35 (CF₃O, s); −70.45 (CF₃, d); −135.2 (1F, m).

(ii) 1,1-Difluoro-2-(4-trifluoromethoxyphenyl)-5-(4-fluoro-3-phenoxyphenyl)pentane from 1,1-difluoro-1-chloro-2-(4-trifluoromethoxyphenyl)-5-(4-fluoro-3-phenoxyphenyl)penta-2,4-diene.

Hydrogenation of 1,1-difluoro-1-chloro-2-(4-trifluoromethoxyphenyl)-5-(4-fluoro-3-phenoxyphenyl)penta-2,4-diene at a hydrogen pressure of 4 atmospheres for 5 hours produced a multi-component mixture of products, one of which was identified as the title compound following reductive removal of the chlorine atom. The products were separated by analytical high pressure liquid chromatography on a Dupont silica column eluted with hexane containing 1% by volume ethyl acetate.

Details for title compound

¹H NMR (CDCl₃) δ (ppm): 1.46 (2H,m); ca 1.7, 1.9 (each 1H, broad m); 2.52 (2H,m); 2.96 (1H,m);5.77 (1H,dt, J=5 Hz and 56 Hz); 6.8–7.4 (12H,m).

¹⁹F NMR (CDCl₃) δ (ppm - relative to CFCl₃): −58.37 (CF₃O,s); ca −121.24 (CF₂H,m); −135.28 (1F,m)

(iii) 1,1-Difluoro-2-(4-ethoxyphenyl)-5-(3-phenoxyphenyl)-pentane from 1,1-difluoro-2-(4-ethoxyphenyl)-5-(3-phenoxyphenyl)penta-2,4-diene.

¹H NMR (CDCl₃) δ (ppm): 1.41 (3H,t); 1.5 (2H,m); 1.6–1.9 (2H,m); 2.55 (2H,m); 2.9 (1H,m); 4.02 (2H,g); 5.75 (1H,dt, J=57 Hz and 5 Hz); 6.7–7.4 (13H,m).

(iv) 1,1-Difluoro-1-chloro-2-(4-ethoxyphenyl)-5-(3phenoxyphenyl)-pentane from 1,1-difluoro-1-chloro-2-(4-ethoxyphenyl)-5-(3-phenoxyphenyl)penta-2,4-diene.

¹H NMR (CDCl₃) δ (ppm): 1.3–1.6 (5H,m); 1.8–2.1 (2H,m); 2.55 (2H,m); 3.27 (1H,dg); 4.02 (2H,g); 6.7–7.4 (13H,m).

Molecular ion: 430, 432 (two peaks due to chlorine isotopes).

In this case, hydrogenation for 4½ hours at 3.5 atmospheres using a Rhodium on alumina catalyst, produced a complex mixture including partially reduced material. Further hydrogenation (4 hours at 3 atmospheres) of the mixture produced two main components which were separated by high pressure liquid chromatography to give the title product and a further reduction product characterised as 1,1-difluoro-2-(4-ethoxyphenyl)-5-(3-phenoxyphenyl)-pentane, resulting from reductive dechlorination. The dechlorinated product was identical with the product obtained in Example 8(iii) above.

(v) 1,1,1-Trifluoro-2-(4-trifluoromethoxyphenyl)-5-[3-(4-chlorophenoxy)phenyl]pentane, from 1,1,1-trifluoro-2-(4-trifluoromethoxyphenyl)-5-[3-(4-chlorophenoxy)phenyl]-penta-2,4-diene ¹H NMR (CDCl₃) δ (ppm): 1.5 (2H, broad m); 1.85 and 2.04 (2H, broad m); 2.58 (2H,m); 3.25 (1H,m); 6.7–7.35 (12H,m)

Molecular ion: 488/490

(vi) 2-(4-Trifluoromethoxyphenyl)-5-(3-phenoxyphenyl)-pentane. This compound was produced by reductive defluorination as the major product during the hydrogenation of 1,1-difluoro-2-(4-trifluoromethoxyphenyl)-5-(3-phenoxyphenyl)-penta-2,4-diene (palladium on charcoal catalyst, 4.3 atmospheres, 2.5 hours). The difluoro and the monofluoro reduction products were identified as minor products.

Characteristic data for major product:

¹H NMR (CDCl₃) δ (ppm): 1.22 (3H,d); 1.4–1.65 (4H,m); 2.55 (2H,m); 2.9 (1H,g); 6.8–7.4 (13H,m)

¹⁹F NMR (CDCl₃) δ (ppm - relative to CFCl₃): −58.4 (CF₃O,s)

Molecular ion: 400

Characteristic data for 1,1-difluoro-2-(4-trifluoromethoxyphenyl)-5-(3-phenoxyphenyl)pentane:

$^1$H NMR (CDCl$_3$) δ (ppm): 1.5 (2H,m); 1.7–2.0 (2H,m); 2.56 (2H,m); 3.0 (1H,m); 5.8 (1H,dt); 6.7–7.4 (13H,m)

$^{19}$F NMR (CDCl$_3$) δ (ppm relative to CFCl$_3$): −58.4 (CF$_3$O,S); −121.2 (CHF$_2$,m)

We claim:

1. A process for the preparation of a compound of formula (I):

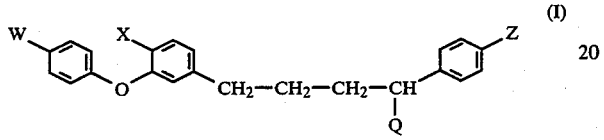

wherein W is hydrogen or halogen, X is hydrogen or fluoro, Q is a group of formula:

wherein R$^1$ is hydrogen, fluoro or chloro and n has a value of one, and Z is halo, alkyl of up to six carbon atoms, alkoxy of up to six carbon atoms, haloalkyl of up to six carbon atoms or haloalkoxy of up to six carbon atoms, which comprises the step of:

(i) Wittig reaction between either (a) a phosphonium salt of formula (III):

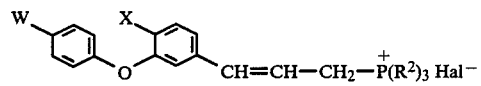

or (b) a phosphonate of formula (IV):

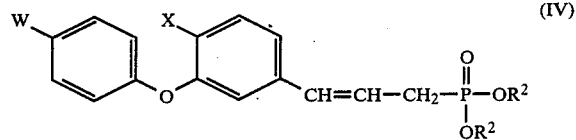

wherein W and X have any of the meanings given hereinbefore, R$^2$ represents alkyl of up to six carbon atoms or aryl, and Hal$^-$ represents a halide anion, and a ketone of formula (VII):

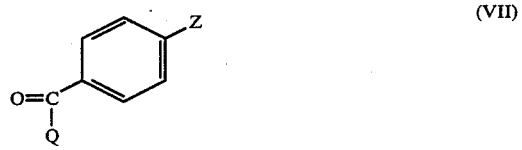

wherein Q and Z have any of the meanings given hereinbefore, in the presence of a strong base, to produce a diene of formula (II):

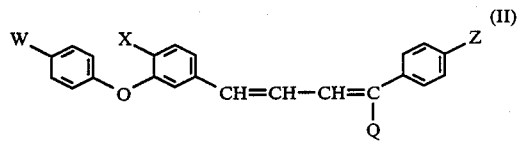

followed by the step of:

(ii) reaction of the diene of formula (II) with hydrogen as a reducing agent in the presence of a catalyst, and at a pressure of from 1.5 to 20 atmospheres to produce the corresponding compound of formula (I):

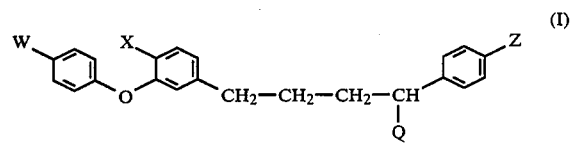

* * * * *